Figure 1:
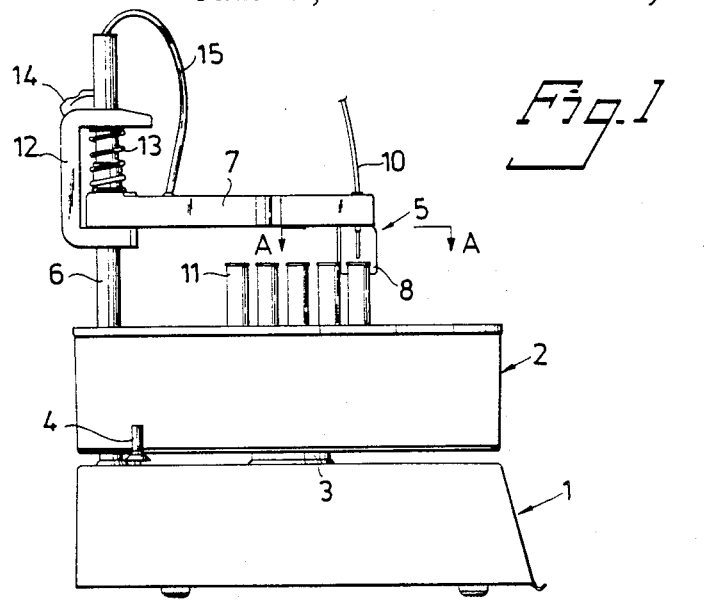

United States Patent [19]

Harström et al.

[11] Patent Number: 4,495,975
[45] Date of Patent: Jan. 29, 1985

[54] SAMPLE TREATMENT DEVICE

[75] Inventors: Karl U. Harström, Lennaholm; Bengt-Åke Nilsson, Upsala, both of Sweden; Richard J. Wheeler, Warren, N.J.

[73] Assignee: Pharmacia AB, Upsala, Sweden

[21] Appl. No.: 420,911

[22] Filed: Sep. 21, 1982

[30] Foreign Application Priority Data

Sep. 22, 1981 [SE] Sweden ............................ 8105590

[51] Int. Cl.³ .............................................. B67D 5/00
[52] U.S. Cl. ...................................... 141/157; 422/64
[58] Field of Search ............... 141/130, 152, 155, 156, 141/157, 159, 160, 167, 94, 98, 192, 268, 270, 279, 283, 284, 360, 361, 362, 141; 73/864.25; 422/63–65, 67, 100

[56] References Cited

U.S. PATENT DOCUMENTS

| 2,827,928 | 3/1958 | Guckel ............................ 141/141 X |
| 3,415,294 | 12/1968 | Kelly ................................ 141/156 X |
| 3,430,495 | 3/1969 | Bürge ................................. 73/864.25 |
| 3,570,555 | 3/1971 | Gilson .................................... 141/1 |
| 3,817,301 | 6/1974 | Van T'Blik ......................... 141/156 |
| 3,945,412 | 3/1976 | Forsström ........................... 141/130 |
| 4,164,244 | 8/1979 | Meier .................................. 141/156 |
| 4,171,715 | 10/1979 | Forsström ........................... 141/130 |
| 4,202,387 | 5/1980 | Upton ................................. 141/360 |

FOREIGN PATENT DOCUMENTS 1017068 1/1966 United Kingdom ............... 141/130

Primary Examiner—Stephen Marcus
Assistant Examiner—Mark Thronson
Attorney, Agent, or Firm—Fred Philpitt

[57] ABSTRACT

A device for treating samples, for example collection of fractions from a chromatographic separation process, comprises a series of test containers (11), a treatment unit (5) and an apparatus (4) for creating relative motion between the test containers and the treatment unit. The treatment unit passes the test containers in sequence and subjects the same to one or more treatment steps. According to the invention the test tubes are detected and their position indicated by a sensor (9) which is arranged to trigger the treatment step or steps when contacting a given area on the respective test container (11), especially by the resilient biasing of a spring (13).

7 Claims, 3 Drawing Figures

SAMPLE TREATMENT DEVICE

The present invention relates to sample treatment devices of the type, in which a series of test containers are movable in relation to a treatment unit, which is arranged to pass the test containers in sequence subjecting the same to one or more treatment steps. Although the invention and the state of the art primarily will be described with regard to fractional collectors used in chromatographic separations, the invention is not limited to this application, but it can be used in any situation when a series of test containers are to be subjected to an arbitrary treatment in the indicated way.

Examples of suitable other fields of application are automatic chemical and immunological analysis systems wherein e.g. a solution is to be supplied to and/or to be withdrawn from a series of test containers. The expression "treatment" is herein not intended to mean only supply and withdrawal of a liquid, but it also includes other types of treatment such as stirring. It is also to be underlined that the treatment step must not necessarily be the same for all of the test containers, but it can be changed in any suitable manner, for example by micro processor control as is well known in the art. The expression "treatment" is also intended to include the case when certain test containers are detected but not subjected to any treatment at all.

A great number of fractional collectors are previously known. A frequently occurring type has a circular cassette for carrying test containers, e.g. test tubes. The test containers may be arranged in concentric circles or, preferably, according to a helical path. The solution to be divided into fractions, for example the eluate from a chromatographic separation column, is passed through a supply tube which is moved to a position above the container which is in turn to be filled. As mentioned above such devices often comprise a programmable unit for controlling the fractionation as desired. The fractionation can, for example, be controlled such that the containers are filled with a certain volume of liquid or such that a component of the eluate, indicated by a peak in the chromatogram, is collected. There is often a very great number of containers in the cassette, and in order to fill the same without wastage, various constructions have been designed for coordinating the movement of the cassette (which is rotatable around its axis) with the movement of a filler head which dispenses the liquid. The filler head may be provided on a arm which is movable above the cassette in the radial direction. A usual solution of this coordination problem is to let a sensing unit follow a track or the like in the cassette, the movements of the sensing unit along the track mechanically controlling the movement of the filler head along the container path. Markings in the tracks indicate the positions of the containers, and the rotational movement of the cassette is stopped for dispensing liquid when the sensing unit reaches such a marking. One such fractional collector is disclosed in e.g. U.S. Pat. No. 3,945,412.

The drawbacks of devices based on this principle for controlling the position of the filler head are obvious. Thus, there is required a mechanical transfer—often very complex—from the sensing unit to the filler head. Further problems are caused by the fact that the filling positions are not directly related to the test containers actually present but to the cassette track with its markings. Because of this the filler head is, for example, unable to detect if any container position by mistake lacks test container, and the solution will in such case be dispensed directly on the cassette and thereby be wasted. For similar reasons the flexibility is reduced as to the possibility of using containers of varying sizes.

U.S. Pat. No. 3,570,555 discloses a device in which means are brought to engage into a container, but the purpose is, on one hand, to drive the cassette forward and, on the other hand, to place the filler head above an adjacent container. For this device to function there is required a complex mechanical driving mechanism, and further that adjacent containers are at essentially the same distance from each other. Further, it does not either appear to be possible to change to containers of a different size without considerable modifications of the device.

It is an object of the present invention to eliminate or reduce these and other problems in the prior art sample treatment devices. The invention in particular aims at providing a simple and inexpensive solution of the problem to place the filler head above the containers without wastage. Another purpose of the invention is to provide a device of the indicated type which makes it possible to use containers of varying dimensions in one and the same cassette while maintaining proper functioning, the changeover to containers of considerably different sizes only requiring change of the container rack of the cassette.

These and other objects of the invention are obtained by means of the features indicated in the subsequent claims and explained in more detail below.

One basic idea of the invention is thus to directly sense the container which is in turn to be treated, and this is applicable both on containers placed in circular or helical paths and on containers placed in parallel rows in a rectangular cassette, etc.

Figure 2:
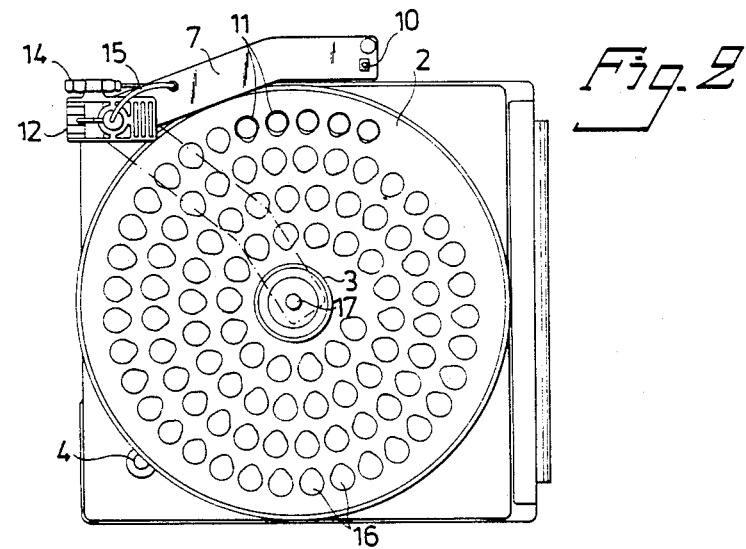
Figure 3:
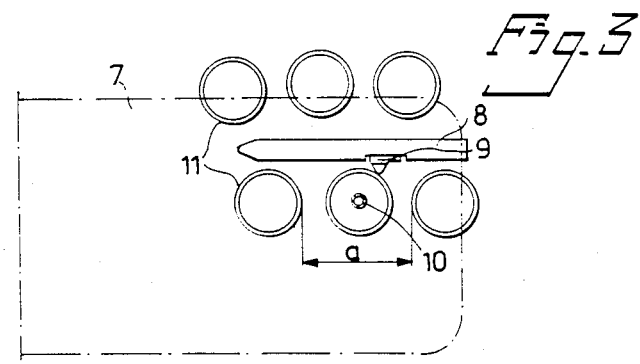

A preferred embodiment of the invention, to which the same however is not limited, will be described with reference to the enclosed drawings in which FIG. 1 is a side elevational view of a sample treatment device according to the invention designed as a fractional collector having a plurality of containers arranged in a helical path, FIG. 2 is a top plan view of the fractional containers shown in FIG. 1, and FIG. 3 is a schematic part sectional view in larger scale taken along A—A in FIG. 1.

The fractional collector which is schematically shown in FIGS. 1 and 2 has a bottom part or support 1, which in conventional manner i.e. contains a motor for driving a test tube cassette 2 and a program unit for controlling the course of the treatments to be performed. The cassette 2 is rotatably journalled on the support 1 by means of a hollow shaft 3, and the rotational movement is in the shown embodiment caused by a drive roller 4 contacting the circumference of the circular cassette. The treatment unit 5 is carried on the support 1 via a vertical carrier rod 6. The treatment unit 5 comprises a horizontal arm 7, one end of which is pivotally supported on the carrier rod 6, whereas its opposite end carries a guide plate 8 having a microswitch 9 disposed thereon and being provided with one or more hoses 10 for supplying eluate to be collected in the test tubes 11. A yoke 12 encloses the arm 7 on the rod 6, and a coil spring 13 is arranged between the top leg of the yoke 12 and the arm 7. The coil spring 13 is attached, on the one hand, to the top portion of the yoke, 12, and, on the other hand, to the arm 7, so that the same by the spring action tends to take the central position shown in dash-dotted lines in FIG. 2.

The yoke 12 is locked against rotation around the rod 6, but it can be displaced along the same and be fixed in arbitrary desired positions by means of a clamping screw 14. A projection on the arm 7 and a corresponding recess in the bottom leg of the yoke 12 (not shown) locks the arm 7 in the outer position shown in full lines in FIG. 2, and the arm 7 can be released from this locked position by removing the locking engagement between the projection and the recess, e.g. by lifting the arm 7.

As is best seen in FIG. 3 the guide plate 8 carried by the arm 7 is arranged essentially tangential to the test tubes 11, and one side edge thereof is preferably bevelled or rounded to facilitate the guiding along the test tubes. The microswitch 9 carried by the guide plate 8 is arranged to be activated when contacting a predetermined area on the respective test container, corresponding to a given position of the filler tube 10 with regard to the test tube. In the specifically shown embodiment, in which the test tubes used are of essentially circular shape, this given area is the one where the switch 9 is essentially tangential to the tube 11 to be treated (or somewhat before this position because of the inertia of the system—see FIG. 3). The breaking signal from the switch 9 is passed to the program unit in the support 1 via leads 15.

The above described device functions essentially in the following manner when used as a fractional collector. A desired number of test tubes 11 are placed in corresponding recesses 16 provided in the cassette 2. The recesses 16 are preferably, in a manner known per se, provided with resilient means making it possible for test tubes of varying sizes to be firmly held therein. The arm 7 is adjusted to a suitable level relative to the particular test tubes used by adjustment of the position of yoke 12 on the rod 6. The arm 7 is then released from its locked outer position (e.g. by lifting), the biasing force of the spring 13 causing the arm to move towards the center 3, 17 of the cassette holder 2. The inward movement of the arm 7 will be stopped when the guide plate 8 contacts the test tubes 11. At the same time the cassette 2 is brought into rotation by the drive roller 4. When the switch 9 during the rotation comes into breaking contact with a test tube (see FIG. 3) an electrical signal is, via the lead 15, sent to the program unit, indicating that the filler tube or tubes 10 are positioned correctly above the test tube to be treated. The program unit then triggers the programmed treatment step, which in the described case means that the driving of the cassette 2 is stopped and a desired amount of solution is allowed to drip into the test tube. After completion of the desired treatment the driving motion is continued, the guide plate 8 guiding the switch 9 into contact with the next tube 11, the treatment procedure being repeated. The process is repeated until the last test tube has been treated (or alternatively until the process is stopped by the program). When the cassette thereafter is driven forward the guide plate 8 will no longer be stopped by any test tube, the result being that the biasing force of the spring 13 will move the arm 7 to the center of the cassette. Any suitable stop means (not shown) can be used to stop the arm 7 in the dash-dotted position in FIG. 2. In this position the filler tube 10 is positioned above an outlet 17 for collecting possibly continuing discharge of liquid from the tube 10, for example washing liquid used for washing the separation column after the fractionation has been terminated.

As mentioned above the treatment step which is triggered by the sensing of the correct position of a test tube by the switch 9 can comprise other measures than supply of liquid. In this context washing of paper discs in immunological analyses can be mentioned as a further example, in which case it is preferred to provide the treatment unit 5 with filling and withdrawal means which can be lowered into the container during the treatment step, liquid alternatingly being supplied and sucked away in a washing process. It is not either always necessary to stop the test tube during the treatment step, but the treatment can in many cases be carried out under continued relative motion between the treatment unit and the test tubes. However the treatment is still triggered by the sensor 9.

According to a preferred embodiment the guide plate 8 has a greater width than the smallest periphery distance (a in FIG. 3) between the outer ones of the three adjacent test tubes 11. By this arrangement one missing tube will not cause the arm 7 to move radially through the "test tube gap" to an inner row or path of test tubes (or to the center). Since it is the direct sensing of a test tube that triggers the treatment step, there will not either be any wastage of solution (or triggering of any other treatment step) in an empty container position. Even if the gap in the test tube path would be greater than the width of the guide plate 8, this would only result in the guide plate contacting the closest interior test tube path, the fractionation continuing in these test tubes. Thus, there will not either be any wastage of solution in this case.

Because of the new and unique way of sensing the position of the test tubes to be treated, i.e. by the sensor 9, carried by the arm 7, directly sensing a tube to be treated, the invention also makes it possible to detect test tubes of different sizes and to correspondingly adjust the treatment step to be performed. Thus, the device can be provided with means (not shown) for detecting the relative radial position of the arm 11 and sending this information to the program unit, which can adjust the treatment step accordingly. For example, this embodiment can be used for dispensing different volumes of liquid into tubes of different sizes. When, for example, a comparatively small test tube 11 (which is to be filled with a comparatively small volume of liquid) is followed by a tube of larger diameter, then a great volume of liquid can be dispensed into the larger tube.

The invention is, of course, not restricted to the embodiment which has been specifically described above and shown in the drawings, but many modifications and variations are possible as to field of use, construction of details, choice of treatment steps, etc.

What we claim is:
1. A sample treatment device comprising:
(a) a plurality of test containers,
(b) a treatment unit,
(c) drive means for creating a relative motion between said test containers and said treatment unit so that the test containers are in turn subjected to one or more treatment steps by said treatment unit,
(d) sensor means arranged for relative motion between said test container and said sensor means and arranged to trigger said one or more treatment steps when said sensor means contacts a given area on a test container,

(e) spring means biasing said sensor means against the test containers, and (f) a guide plate carrying said sensor means and extending essentially in the direction of relative motion between the test containers and the sensor means, said sensor means being arranged to stop, at least for certain test containers, the relative motion between a test container and the treatment unit upon contact with said given area on the test container, and said test containers are carried by a rotatable cassette and are arranged along a helical path thereon.

2. A device according to claim 1 wherein said treatment unit comprises an essentially horizontal arm, one end of which is pivotally mounted on an essentially vertical shaft and the other end of which carries said sensor means, said biasing spring means comprising a spring acting between said shaft and said arm providing said biasing force.

3. A device according to claim 2 wherein said cassette is an essentially circular test container cassette and wherein said biasing spring means tends to move said arm from a starting position, in which it is at the periphery of said cassette, to an end position, in which it is at the centre of said cassette.

4. A device according to claim 1 wherein said sensor means comprises a contact switch.

5. A device according to claim 4 wherein said contact switch is a microswitch.

6. A device according to claim 1 wherein said guide plate has a sufficient length in the direction of the relative motion between the test containers and the sensor means, so that it cannot pass through a gap corresponding to a missing tube.

7. A device according to claim 1 wherein said sensor means are connected to a program unit, which starts said at least one treatment steps upon indication from said sensor means.

* * * * *